United States Patent [19]

Zinnen

[11] Patent Number: 5,159,131
[45] Date of Patent: Oct. 27, 1992

[54] ZEOLITIC PARA-XYLENE SEPARATION WITH INDAN AND INDAN DERIVATIVES AS HEAVY DESORBENT

[75] Inventor: Hermann A. Zinnen, Summit, N.J.

[73] Assignee: UOP, Des Plaines, Ill.

[21] Appl. No.: 812,261

[22] Filed: Dec. 23, 1991

[51] Int. Cl.$^5$ ............................................. C07C 7/12
[52] U.S. Cl. .................................. 585/828; 585/825; 585/826; 585/855
[58] Field of Search ................. 585/825, 826, 828, 855

[56] References Cited

U.S. PATENT DOCUMENTS

| | | | |
|---|---|---|---|
| 2,985,589 | 5/1961 | Broughton et al. | 210/34 |
| 3,040,777 | 6/1962 | Carson et al. | 137/625.15 |
| 3,422,848 | 1/1969 | Liebman et al. | 137/625.15 |
| 3,626,020 | 12/1971 | Neuzil | 260/674 SA |
| 3,663,638 | 5/1972 | Neuzil | 260/674 SA |
| 3,665,046 | 5/1972 | De Rosset | 260/674 SA |
| 3,668,266 | 6/1972 | Chen et al. | 260/674 |
| 3,686,342 | 8/1972 | Neuzil | 260/674 SA |
| 3,700,744 | 10/1972 | Berger et al. | 260/668 A |
| 3,706,812 | 12/1972 | De Rosset et al. | 260/674 SA |
| 3,723,302 | 3/1973 | Pharis et al. | 208/310 |
| 3,734,974 | 5/1973 | Neuzil | 260/674 SA |
| 3,894,109 | 7/1975 | Rosback | 260/674 SA |
| 3,997,620 | 12/1976 | Neuzil | 260/674 SA |
| 4,014,949 | 3/1977 | Hedge | 260/674 SA |
| 4,159,284 | 6/1979 | Seko et al. | 585/478 |
| 4,313,015 | 1/1982 | Broughton | 585/828 |
| 4,402,832 | 9/1983 | Gerhold | 210/659 |
| 4,478,721 | 10/1984 | Gerhold | 210/659 |
| 4,642,397 | 2/1987 | Zinnen et al. | 568/934 |
| 4,778,946 | 10/1988 | Hulme et al. | 595/828 |
| 4,864,069 | 9/1989 | Zinnen | 585/828 |
| 4,886,930 | 12/1989 | Zinnen | 585/828 |
| 5,012,038 | 4/1991 | Zinnen | 585/828 |
| 5,057,643 | 10/1991 | Zinnen | 585/828 |

Primary Examiner—Asok Pal
Assistant Examiner—Nhat Phan
Attorney, Agent, or Firm—Thomas K. McBride; John F. Spears, Jr.; Jack H. Hall

[57] ABSTRACT

A chromatographic process able to separate para-xylene from $C_8$ isomers and $C_9$ aromatics. In the process, the para-xylene-containing feed mixture is contacted with an X zeolite adsorbent having barium or barium and potassium ions, at exchangeable cationic sites. The para-xylene components are selectively adsorbed onto the adsorbent. The non-adsorbed feed is then removed from the adsorbent and the para-xylene recovered by desorption with indan or an alkyl derivative of indan. Any $C_9$ aromatic hydrocarbons and the other xylene isomers in the raffinate can be separated from these heavy desorbents by fractionation of the raffinate and the desorbent can be recycled to the process.

5 Claims, 1 Drawing Sheet

ZEOLITIC PARA-XYLENE SEPARATION WITH INDAN AND INDAN DERIVATIVES AS HEAVY DESORBENT

FIELD OF THE INVENTION

The field of art to which the claimed invention pertains is hydrocarbon separation. More specifically, the invention relates to a process for separating para-xylene from a feed mixture comprising at least two xylene isomers, including the para-isomer, which process employs a zeolitic adsorbent and particular desorbents. It is particularly advantageous in a process in which the feed contains $C_9$ aromatic hydrocarbon.

BACKGROUND OF THE INVENTION

In numerous processes described in the patent literature, for example U.S. Pat. Nos. 3,626,020 to Neuzil, 3,663,638 to Neuzil, 3,665,046 to deRosset, 3,668,266 to Chen et al., 3,686,342 to Neuzil et al., 3,700,744 to Berger et al., 3,734,974 to Neuzil, 3,894,109 to Rosback, 3,997,620 to Neuzil and 4,014,949 to Hedge, particular zeolitic adsorbents are used to separate the para isomer of dialkyl substituted monocyclic aromatics from the other isomers, particularly para-xylene from other xylene isomers. Many of the above patents use benzene, toluene, or p-diethylbenzene as the desorbent. P-diethylbenzene (p-DEB) has become a commercial standard for this separation. However, p-DEB is a "heavy" desorbent (higher boiling than p-xylene) which suffers in the process for separating p-xylene from feed mixtures containing $C_9$ aromatics, such as crystallizer feedstocks because the boiling point of p-DEB is too close to the boiling point of $C_9$ aromatics in the feed. Because the $C_9$ aromatics are difficult to separate from p-DEB by simple fractionation, the $C_9$ aromatics would gradually build up in the desorbent, which must be recycled for economic reasons. In the commercial process for recovering p-xylene from feed mixtures containing isomers, therefore, it has been necessary to reduce $C_9$ aromatics in the feed to below about 0.1% prior to the adsorptive separation of p-xylene. This is usually done by distillation in a so-called xylene splitter column. Of course, substantial costs associated with this practice, such as capital costs of the xylene splitter and utilities necessary to achieve substantially complete removal of the $C_9$ aromatics, could be reduced greatly or eliminated if it were not necessary to first remove $C_9$ aromatics.

U.S. Pat. No. 3,686,342, supra, mentions other aromatic hydrocarbons as a possible heavy desorbent for the para-xylene separation process. That reference clearly states that p-DEB is the best desorbent for the separation and, further, does not address the problem that the preferred desorbents may have in separating feeds containing $C_9$ aromatics.

More recently, in Zinnen et al. U.S. Pat. Nos. 4,886,930; 4,864,069; 5,012,038 and 5,057,643, other "heavy" desorbents, e.g., diethyltoluene, tetralin and tetralin derivatives, have been disclosed for a process for separating para-xylene when the feed mixtures contain higher boiling aromatic hydrocarbons, such as $C_9$ aromatics, $C_{10}$ aromatics, etc. However, these materials are not readily available except synthetically produced. Therefore, a higher boiling point material, i.e., "heavy desorbent", that meets the selectivity requirements for desorbents can be used with feed mixtures containing $C_9$ aromatics and is available from natural, rather than synthetic, sources, such as coal tar distillates, etc., is desirable.

Indan has been proposed as desorbent for the separation of ethylbenzene from para-xylene-depleted $C_8$ aromatic feedstreams in U.S. Pat. No. 4,778,946. The adsorbent disclosed was potassium-exchanged Y zeolite. There is no suggestion therein of using indan as the desorbent for the separation of p-xylene from other $C_8$ isomers.

It is also known that crystalline aluminosilicates or zeolites are used in adsorption separations of various mixtures in the form of agglomerates having high physical strength and attrition resistance. Methods for forming the crystalline powders into such agglomerates include the addition of an inorganic binder, generally a clay comprising a silicon dioxide and aluminum oxide, to the high purity zeolite powder in wet mixture. The blended clay zeolite mixture is extruded into cylindrical type pellets or formed into beads which are subsequently calcined in order to convert the clay to an amorphous binder of considerable mechanical strength. As binders, clays of the kaolin type, water permeable organic polymers or silica are generally used.

The invention herein can be practiced in fixed or moving adsorbent bed systems, but the preferred system for this separation is a countercurrent simulated moving bed system, such as described in Broughton U.S. Pat. No. 2,985,589, incorporated herein by reference. Cyclic advancement of the input and output streams can be accomplished by a manifolding system, which are also known, e.g., by rotary disc valves shown in U.S. Pat. Nos. 3,040,777 and 3,422,848. Equipment utilizing these principles are familiar, in sizes ranging from pilot plant scale (deRosset U.S. Pat. No. 3,706,812) to commercial scale in flow rates from a few cc per hour to many thousands of gallons per hour.

The invention may also be practiced in a cocurrent, pulsed batch process, like that described in U.S. Pat. No. 4,159,284 or in a cocurrent, pulsed continuous process, like that disclosed in Gerhold U.S. Pat. Nos. 4,402,832 and 4,478,721.

Also, in some cases illustrated herein, it is necessary to remove three product streams in order to obtain a desired product intermediate in adsorption strength from an extract and a raffinate stream. This intermediate stream can be termed a second raffinate stream, as in U.S. Pat. No. 4,313,015 or a second extract stream, as in U.S. Pat. No. 3,723,302, both incorporated herein by reference, the latter incorporating abandoned application Ser. No. 100,105 filed Dec. 21, 1970. This case pertains when a contaminating component in the feed, such as p-ethyltoluene, is more strongly adsorbed than the desired product, p-xylene. It is not always necessary to remove p-ethyltoluene from p-xylene, e.g., where terephthalic acid is the final product of the oxidation of p-xylene, since oxidation of p-ethyltoluene results in the same product. However, if it is desired to keep the concentration of the contaminating component in the product as low as possible, a first extract is taken off, high in concentration of the desired component and lower in the contaminating product followed by a second extract, withdrawn at a point in zone 3 between the desorbent inlet and the first extract point, containing a high concentration of the contaminant and a lower concentration of the desired product. It is not necessary, however, to use a second desorbent, if the desorbent is able to first desorb the lightly held product and then desorb the remaining more strongly held contaminants, as disclosed in the aforementioned abandoned application. If separation of the contaminating component in high concentrations and purity is desired, this can be achieved by withdrawing a second extract in the cocurrent pulsed batch process mentioned above.

The functions and properties of adsorbents and desorbents in the chromatographic separation of liquid components are well-known, but for reference thereto, Zinnen et al. U.S. Pat. No. 4,642,397 is incorporated herein.

I have discovered a process for employing a zeolite adsorbent for the separation of p-xylene from its isomers and, particularly, a desorbent which is a substantial improvement in a process for separating xylene isomers where the feed mixture also contains $C_9$ aromatic impurities.

SUMMARY OF THE INVENTION

In brief summary, the invention is a chromatographic process for separating p-xylene from a feed mixture comprising p-xylene, one or more additional xylene isomers (including ethylbenzene) and may also contain $C_9$ aromatic hydrocarbons, comprising contacting said feed mixture with an X zeolite exchanged with barium or barium and potassium ions at exchangeable cationic sites to effect the selective adsorption of said p-xylene and produce a raffinate comprising the other xylene isomers, including ethylbenzene, and $C_9$ aromatics. P-xylene is recovered thereafter by contacting the resulting para-xylene rich adsorbent with a desorbent comprising indan or an alkyl derivative of indan or mixtures thereof. These desorbents, especially the alkyl derivatives (Table 1) are higher boiling than the $C_9$ aromatics, making it possible to separate the $C_9$ aromatics from the desorbent by fractionation so that the desorbent can be reused in the process without building up $C_9$ aromatics in the recycled desorbent.

TABLE 1

| Desorbent | Literature (1) Normal BP | Calculated (2) Normal BP |
|---|---|---|
| indan | 177.8 | 175.2 |
| 1-methyl indan | 190.6 | 193.4 |
| 2-methyl indan | 191.4 | 193.4 |
| 4-methyl indan | 205.3 | 203.1 |
| 5-methyl indan | 202.8 | 203.1 |
| 1-ethyl indan | 222 | 216.3 |
| 5-hexyl indan | 292.1 | 317.5 |
| 1,1-dimethyl indan | 191 | 216.5 |
| 1,2-dimethyl indan | — | 211.6 |
| 4,6-dimethyl indan | — | 230.9 |
| 1,1,4-trimethyl indan | — | 244.4 |
| 1,4,7-trimethyl indan | — | 249.1 |
| 4,5,7-trimethyl indan | — | 258.8 |

(1) CRC Handbook of Data on Organic Compounds, Vol. 1, pp 767–768, Handbook Consultants Company, Inc., Asheville, NC, 1985.
(2) Joback's Method. cf. R. Reid, J. Prausnitz, B. Poling, "The Properties of Gases and Liquids, 4th Edition, McGraw-Hill, New York, 1987.

Especially preferred are the indan derivatives boiling above about 190° C., i.e., methyl indan, dimethyl indan, ethyl indan, propyl indan, isopropyl indan, hexyl indan and trimethyl indan.

Figure 1:
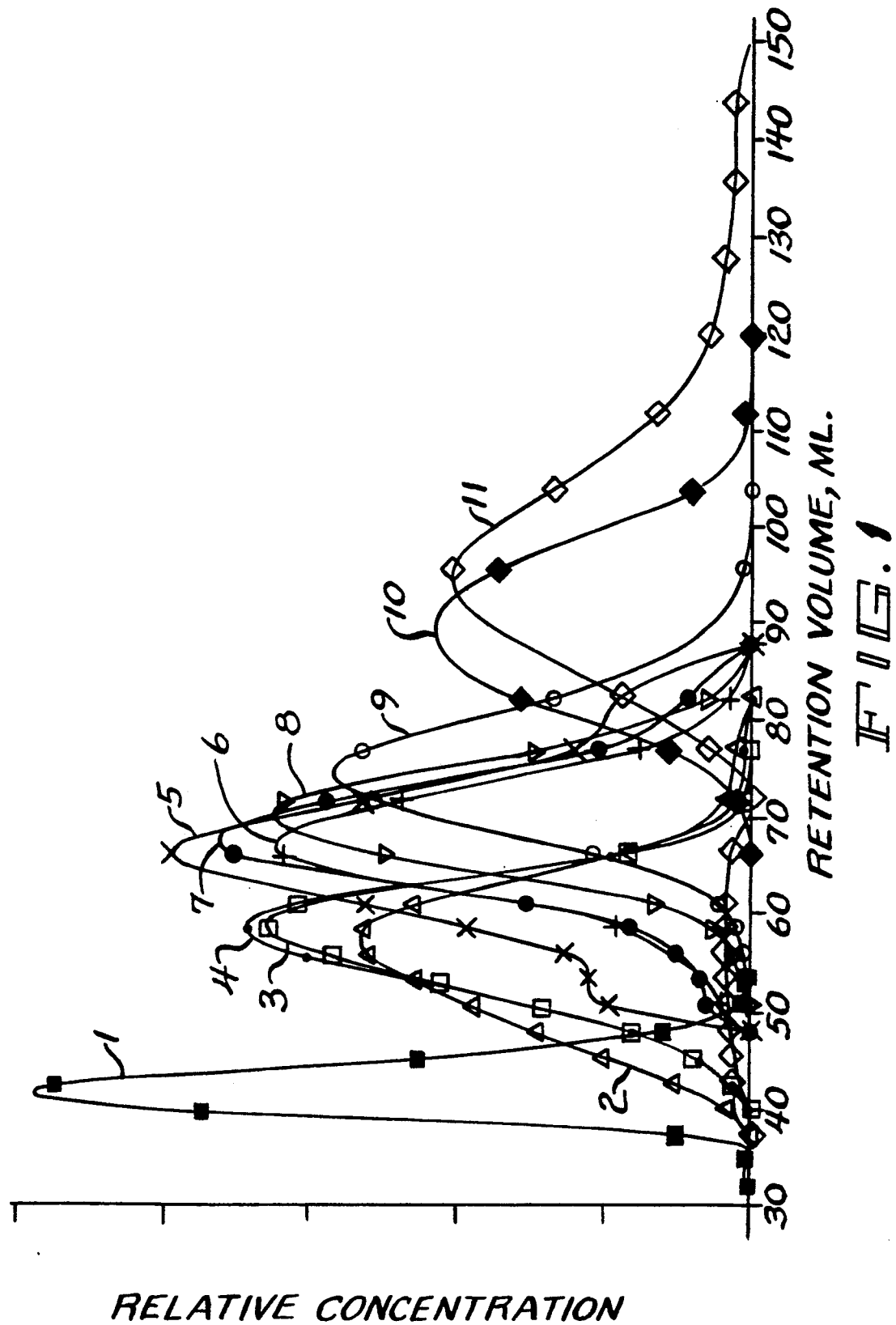
FIG. 1 is a chromatographic representation of the separation of p-xylene from a mixture of xylene isomers and $C_9$ aromatics with a barium-exchanged X zeolite and a desorbent comprising a 30/70 mixture of indan and n-heptane.

In the FIGURE, numerals are used to indicate the component lines in the graph of relative concentrations vs. retention volume (ml.) as follows: the tracer 1; mesitylene 2; m-xylene 3; o-xylene 4; 1,2,3-trimethylbenzene 5; 1,2,4-trimethylbenzene 6; n-propylbenzene 7; ethylbenzene 8; cumene 9; p-xylene 10 and p-ethyltoluene 11.

DETAILED DESCRIPTION OF THE INVENTION

Adsorbents to be used in the process of this invention comprise specific crystalline aluminosilicates or molecular sieves, namely X zeolites exchanged with barium or barium and potassium ions at the exchangeable sites. The zeolites have known cage structures in which the alumina and silica tetrahedra are intimately connected in an open three-dimensional network to form cage-like structures with window-like pores. The tetrahedra are cross-linked by the sharing of oxygen atoms with spaces between the tetrahedra occupied by water molecules prior to partial or total dehydration of this zeolite. The dehydration of the zeolite results in crystals interlaced with cells having molecular dimensions and thus, the crystalline aluminosilicates are often referred to as "molecular sieves" when the separation which they effect is dependent essentially upon differences between the sizes of the feed molecules as, for instance, when smaller normal paraffin molecules are separated from larger isoparaffin molecules by using a particular molecular sieve. In the process of this invention, however, the term "molecular sieves", although widely used, is not strictly suitable since the separation of specific aromatic isomers is apparently dependent on differences in electrochemical attraction of the different isomers and the adsorbent rather than on pure physical size differences in the isomer molecules.

In hydrated form, the crystalline aluminosilicates encompass type X zeolites which are represented by Formula 1 below in terms of moles of oxides:

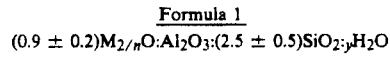
Formula 1
$$(0.9 \pm 0.2)M_{2/n}O:Al_2O_3:(2.5 \pm 0.5)SiO_2:yH_2O$$

where "M" is a cation having a valence of not more than 3 which balances the electrovalence of the tetrahedra and is generally referred to as an exchangeable cationic site, "n" represents the valence of the cation, and "y", which represents the moles of water, is a value up to about 9 depending upon the identity of "M" and the degree of hydration of the crystal. As noted from Formula 1, the $SiO_2/Al_2O_3$ mole ratio is $2.5\pm0.5$. The cation "M" may be monovalent, divalent or trivalent cations or mixtures thereof. In the separation of the invention, "M" is barium or a mixture of barium and potassium.

Typically, adsorbents used in separative processes contain the crystalline material dispersed in an amorphous, inorganic matrix or binder, having channels and cavities therein which enable liquid access to the crystalline material. Silica, alumina, clay or mixtures thereof are typical of such inorganic matrix materials. The binder aids in forming or agglomerating the crystalline particles which otherwise would comprise a fine powder. The adsorbent may thus be in the form of particles such as extrudates, aggregates, tablets, macrospheres or granules having a desired particle range, preferably from about 16 to about 60 mesh (Standard U.S. Mesh) (1.9 mm to 250 microns).

Feed mixtures which can be utilized in the process of this invention will comprise para-xylene, at least one other $C_8$ aromatic isomer, and may also contain one or more $C_9$ aromatics as impurities. Mixtures containing substantial quantities of para-xylene and other $C_8$ aromatic isomers and $C_9$ aromatics generally are produced by reforming and isomerization processes, processes which are well known to the refining and petrochemical arts. Many of the $C_9$ aromatics have boiling points in the range of 160°–170° C. and cannot be easily removed by distillation from the standard desorbent, p-diethylbenzene. In the prior commercial process, therefore, the $C_9$'s were usually removed from the feed by distillation before the adsorptive separation and consequent contact with the normal desorbent. I have discovered desorbents which can be easily separated from the $C_9$ aromatics by fractionation and do not require the large column and quantity of utilities to pretreat the feed, resulting in substantial cost savings.

Reforming processes can provide feed mixtures for the process of this invention. In reforming processes, a naphtha feed is contacted with a platinum-halogen-containing catalyst at severities selected to produce an effluent containing $C_8$ aromatic isomers. Generally, the reformate is then fractionated to concentrate the $C_8$ aromatic isomers in a $C_8$ fraction which will contain the $C_8$ aromatic isomers as well as $C_8$ nonaromatics and $C_9$ aromatics. Feed mixtures for the process of this invention may also be obtained from isomerization and transalkylation processes. Xylene mixtures which are deficient in one or more isomers can be isomerized, at isomerization conditions, to produce an effluent containing $C_8$ aromatic isomers, e.g., enriched in p-xylene, as well as $C_8$ non-aromatics and $C_9$ aromatics. The $C_9$ aromatic content of isomerized xylene isomers can be as much as 1–2 wt. % depending on isomerization conditions. Likewise, transalkylation of mixtures of $C_7$ and $C_9$ aromatics produces xylene isomers. In all of these catalytic routes, the xylene splitter column must be employed to remove $C_9$ aromatics from $C_8$ aromatics before conventional adsorptive xylene separation methods can be employed. Thus, the feed mixtures to the process of this invention can contain quantities of $C_9$ aromatics and may also contain quantities of straight or branched chain paraffins, cycloparaffins, or olefinic material. It is preferable to have these quantities at a minimum amount in order to prevent contamination of products from this process by materials which are not selectively adsorbed or separated by the adsorbent. Preferably, the above-mentioned contaminants should be less than about 20% of the volume of the feed mixture passed into the process.

To separate the para-xylene from a feed mixture containing para-xylene, at least one other $C_8$ aromatic and $C_9$ aromatics, the mixture is contacted with the adsorbent at adsorption conditions and the para-xylene (and para-ethyltoluene, if present) is more selectively adsorbed and retained by the adsorbent while the other components are relatively unadsorbed and are removed from the interstitial void spaces between the particles of adsorbent and from the surface of the adsorbent. The adsorbent containing the more selectively adsorbed para-xylene is referred to as a "rich" adsorbent-rich in the more selectively adsorbed para-xylene. The para-xylene is then recovered from the rich adsorbent by contacting the rich adsorbent with a desorbent material at desorption conditions.

In this process, which employs zeolitic adsorbents and which is generally operated continuously at substantially constant pressures and temperatures to ensure liquid phase, the desorbent material relied upon must be judiciously selected to satisfy several criteria. First, the desorbent material should displace an extract component from the adsorbent with reasonable mass flow rates without itself being so strongly adsorbed as to unduly prevent the extract component from displacing the desorbent material in a following adsorption cycle. Secondly, the desorbent material must be compatible with the particular adsorbent and the particular feed mixture. More specifically, they must not reduce or destroy the critical selectivity of the adsorbent for an extract component with respect to the raffinate component or react chemically with the feed components. Desorbent materials should additionally be easily separable from the feed mixture that is passed into the process. Both the raffinate components and the extract components are typically removed from the adsorbent in admixture with desorbent material and without a method of separating at least a portion of desorbent material, the purity of the extract product and the raffinate product would not be very high nor would the desorbent material be available for reuse in the process. It is, therefore, contemplated that the desorbent material used in this process will have a substantially higher average boiling point than that of the feed mixture or any of its components, i.e., more than about 5° C. difference, to allow separation of at least a portion of the desorbent material from feed components in the extract and raffinate streams by simple fractional distillation, thereby permitting reuse of desorbent material in the process.

Finally, desorbent materials should be readily available and reasonable in cost. However, a suitable desorbent or desorbents for a particular separation with specific adsorbent are not always predictable. In the preferred isothermal, isobaric, liquid-phase operation of the process of this invention, when the feed material to the separation process contains more than about 0.1 wt. % $C_9$ aromatics, I have found that a desorbent material comprising indan or alkyl derivatives of indan or mixtures thereof will desorb the extract from the adsorbent and can be separated from $C_9$'s by distillation.

Suitable alkyl-substituted derivatives of indan include methyl indan, ethyl indan, dimethyl indan, propyl indan, isopropyl indan, hexyl indan, trimethyl indan, etc. Mixtures of indan with one or more of these derivatives, as well as mixtures of these derivatives also may be used with good results. All position isomers and mixtures are intended to be included when any indan derivative is referred to herein.

Adsorption conditions will include a temperature range of from about 20° to about 250° C. with about 60° to about 200° C. being more preferred and a pressure just sufficient to maintain liquid phase, which may be from about atmospheric to 600 psig. Desorption conditions will include the same range of temperatures and pressure as used for adsorption conditions.

A dynamic testing apparatus is employed to test various adsorbents and desorbent material with a particular feed mixture to measure the adsorbent characteristics of adsorptive capacity and exchange rate. The apparatus consists of a helical adsorbent chamber of approximately 70 cc volume having inlet and outlet portions at opposite ends of the chamber. The chamber is contained within a temperature control means and, in addition, pressure control equipment is used to operate the chamber at a constant predetermined pressure. Quantitative and qualitative equipment, such as refractometers, polarimeters, chromatographs, etc., can be attached to the outlet line of the chamber and used to analyze, "on-stream", the effluent stream leaving the adsorbent chamber.

A pulse test, performed using this apparatus and the following general procedure, is used to determine data, e.g., selectivities, for various adsorbent systems. The adsorbent is filled to equilibrium with a particular desorbent by passing the desorbent material through the adsorbent chamber. At a convenient time, a pulse of feed containing known concentrations of a tracer and of a particular extract component or of a raffinate component, or both, all diluted in desorbent material is injected for a duration of several minutes. Desorbent flow is resumed, and the tracer and the extract and raffinate components are eluted as in a liquid-solid chromatographic operation. The effluent can be analyzed by on-stream chromatographic equipment and traces of the envelopes of corresponding component peaks developed. Alternatively, effluent samples can be collected periodically and later analyzed separately by gas chromatography.

From information derived from the test, adsorbent performance can be rated in terms of void volume, retention volume for an extract or a raffinate component, and the rate of desorption of an extract component from the adsorbent and selectivity. Void volume is the non-selective volume of the adsorbent, which is expressed by the amount of desorbent pumped during the interval from initial flow to the center of the peak envelope of the tracer. The net retention volume (net) of an extract or a raffinate component may be characterized by the distance between the center of the peak envelope (gross retention volume) of the extract or raffinate component and the center of the peak envelope (void volume) of the tracer component or some other known reference point. It is expressed in terms of the volume in cubic centimeters of desorbent material pumped during this time interval represented by the distance between the peak envelopes. The rate of exchange or desorption rate of an extract component with the desorbent material can generally be characterized by the width of the peak envelopes at half intensity. The narrower the peak width, the faster the desorption rate. The desorption rate can also be characterized by the distance between the center of the tracer peak envelope and the disappearance of an extract component which has just been desorbed. This distance is again the volume of desorbent material pumped during this time interval. Selectivity, $\beta$, is determined by the ratio of the net retention volumes of the more strongly adsorbed component to each of the other components.

The following non-limiting examples are presented to illustrate the process of the present invention and are not intended to unduly restrict the scope of the claims attached hereto.

EXAMPLE I

In this experiment, a pulse test, using the apparatus as described above, was performed to evaluate the ability of the present invention to separate para-xylene (b.p. 138° C.) from the other xylene isomers and ethylbenzene (b.p.'s from 136°–145° C.) and from $C_9$ aromatics. The adsorbent used was an X faujasite exchanged with barium, dried to yield a loss upon ignition (LOI) of 4.1 at 500° C. mixed with an amorphous clay binder.

For each pulse test, the column was maintained at a temperature of 150° C. and at a pressure of approximately 165 psig so as to maintain liquid-phase operations. Gas chromatographic analysis equipment was attached to the column effluent stream in order to determine the composition of the effluent material at given time intervals. The feed mixture employed for each test was 5 ml of a mixture containing 0.25 ml each of the xylene isomers and ethylbenzene and each of the following $C_9$ aromatics: cumene, n-propylbenzene, p-ethyltoluene, mesitylene, 1,2,4-trimethylbenzene and 1,2,3-trimethylbenzene. Normal nonane (0.25 cc) was used as a tracer and 2.75 cc desorbent material was added to the feed. The desorbent was indan which was diluted with 70% heptane to increase the retention time in order to make the results more precise. The operations taking place for the test were as follows: The desorbent material was run continuously at a rate of about 1.33 cc per minute. At some convenient time interval, the desorbent was stopped and the feed mixture was injected into the column over a 3.8 minute interval. The desorbent stream was then resumed and continued to pass into the adsorbent column until all of the feed aromatics had been eluted from the column as determined by chromatographic analysis of the effluent material leaving the adsorption column.

The results of the tests shown in Table 2 and the chromatographic tracing of FIG. 1 illustrate the invention. The table lists the gross retention volume (GRV) and net retention volume (NRV) for each component of the feed, the boiling points (b.p.) of the $C_9$ aromatics in the feed and the selectivity, $\beta$, for each component with respect to the reference, p-xylene.

TABLE 2

| Component | B.P. | Gross Retention Volume (ml) | Net Retention Volume (ml) | Selectivity $\beta$ |
|---|---|---|---|---|
| n-$C_9$ | | 41.9 | 0.0 | ∞ |
| Mesitylene | 164 | 55.9 | 13.9 | 3.45 |
| m-Xylene | | 58.0 | 16.1 | 2.98 |
| o-Xylene | | 58.1 | 16.1 | 2.97 |
| 1,2,3-Trimethylbenzene | 176.1 | 66.5 | 24.5 | 1.96 |
| 1,2,4-Trimethylbenzene | 169 | 67.9 | 25.9 | 1.85 |
| n-Propylbenzene | | 68.5 | 26.5 | 1.81 |
| Ethylbenzene | | 70.3 | 28.4 | 1.69 |
| Cumene | 152 | 75.0 | 33.1 | 1.44 |
| p-Xylene | | 89.8 | 47.9 | 1.00 |
| p-Ethyltoluene | | 95.8 | 53.8 | 0.89 |

What is claimed is:

1. A process for separating p-xylene from a feed mixture comprising p-xylene and at least one other isomer of xylene which process comprises contacting said mixture with an adsorbent comprising an X zeolite containing barium or barium and potassium ions at exchangeable cationic sites at adsorption conditions to effect the selective adsorption of said p-xylene by said adsorbent and to produce a raffinate stream comprising said other xylene isomers and contacting said adsorbent with a desorbent comprising indan or an alkyl-substituted indan at desorption conditions to effect the removal of p-xylene from said adsorbent as an extract stream.

2. The process of claim 1 wherein said desorbent is selected from the group consisting of methyl indan, ethyl indan, hexyl indan, dimethyl indan, propyl indan, isopropyl indan and trimethyl indan.

3. The process of claim 1 wherein said feed mixture additionally comprises $C_9$ aromatic hydrocarbons.

4. The process of claim 2 wherein said adsorbent is an X zeolite is exchanged with barium at said exchangeable sites.

5. The process of claim 1 wherein said desorbent comprises indan.

* * * * *